United States Patent [19]

Brayer et al.

[11] Patent Number: 5,304,653
[45] Date of Patent: Apr. 19, 1994

[54] ALPHA-METHYLENE-5-THIAZOLACETIC ACID ESTERS

[75] Inventors: Jean-Louis Brayer, Nanteuil Le Haudoin; Jean-Pierre Demoute, Neuilly Plaisance; Gilles Mourioux, Gemenos, all of France

[73] Assignee: Roussel-Uclaf, France

[21] Appl. No.: 957,284

[22] Filed: Oct. 6, 1992

Related U.S. Application Data

[62] Division of Ser. No. 851,926, Mar. 16, 1992, Pat. No. 5,210,093.

[30] Foreign Application Priority Data

Mar. 21, 1991 [FR] France ................. 91 03432

[51] Int. Cl.$^5$ ........................... C07D 777/30
[52] U.S. Cl. ................................ 548/193
[58] Field of Search ...................... 548/187

[56] References Cited

U.S. PATENT DOCUMENTS 5,166,167 11/1992 Brayer ..................... 514/365

Primary Examiner—Robert Gerstl
Attorney, Agent, or Firm—Bierman and Muserlian

[57] ABSTRACT

A compound of the formula

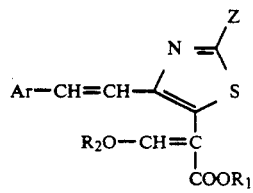

wherein Ar is phenyl optionally substituted with at least one member of the group consisting of halogen, methylenedioxy, phenyl, phenoxy, —$CF_3$ and alkyl, alkoxy and alkylthio of 1 to 6 carbon atoms, Z is selected from the group consisting of hydrogen, chlorine, —$CF_3$ and alkyl, alkoxy and alkylthio of 1 to 6 carbon atoms, $R_1$ and $R_2$ are individually alkyl of 1 to 6 carbon atoms and the exocyclic double bonds independently have (E) or (Z) geometry having fungicidal activity and a process for their preparation.

1 Claim, No Drawings

ALPHA-METHYLENE-5-THIAZOLACETIC ACID ESTERS

This is a division of Ser. No. 851,926 filed Mar. 16, 1992; now U.S. Pat. No. 5,210,093.

It is an object of the invention to provide the novel compounds of formula I and a novel process and intermediates for their preparation.

It is another object of the invention to provide novel fungicidal compositions and a novel method of combatting fungi.

These and other objects and advantages of the invention will become obvious from the following detailed description.

THE INVENTION

The novel compounds of the invention have the formula

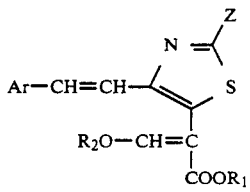

wherein Ar is phenyl optionally substituted with at least one member of the group consisting of halogen, methylenedioxy, phenyl, phenoxy, —$CF_3$ and alkyl, alkoxy and alkylthio of 1 to 6 carbon atoms, Z is selected from the group consisting of hydrogen, chlorine, —$CF_3$ and alkyl, alkoxy and alkylthio of 1 to 6 carbon atoms, $R_1$ and $R_2$ are individually alkyl of 1 to 6 carbon atoms and the exocyclic double bonds independently have (E) or (Z) geometry.

Examples of alkyl and alkoxy of 1 to 6 carbon atoms are methyl, ethyl, propyl, isopropyl, butyl, isobutyl, (R)-sec.-butyl, (S)-sec.butyl, tert.-butyl, methoxy, ethoxy, propoxy, isopropoxy, butoxy, isobutoxy, (R)-sec.-butoxy, (S)-sec.-butoxy and tert.-butoxy. Examples of alkylthio of 1 to 6 carbon atoms are methylthio, ethylthio, propylthio, isopropylthio, butylthio, isobutylthio, (R)-sec.-butylthio, (S)-sec.-butylthio and tert.-butylthio.

Examples of Ar are phenyl optionally substituted by at least one halogen such as 2-bromo-phenyl, 3-bromophenyl, 4-bromo-phenyl, 2-chloro-phenyl, 3-chlorophenyl, 4-chloro-phenyl, 2,6-dichloro-phenyl, 2,3,5-trichloro-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 2,6-difluoro-phenyl, 3,4-difluorophenyl, 3,5-difluoro-phenyl, 2,3,5,6-tetrafluoro-phenyl, 2,3,4,5,6-pentafluorophenyl, 2-chloro 6-fluoro-phenyl or 3-chloro 4-fluoro-phenyl.

When Ar is phenyl substituted by at least one alkyl, examples are ortho-, meta- or para-tolyl, 2,4-dimethyl phenyl or mesityl.

When Ar is phenyl substituted by at least one alkoxy, examples are 2-methoxy-phenyl, 3-methoxy-phenyl, 4-methoxy-phenyl, 4-ethoxy-phenyl, 4-butoxy-phenyl, 2,4-dimethoxy-phenyl or 3,4,5-trimethoxy-phenyl.

When Ar is phenyl substituted by at least one alkylthio, an example is 4-methylthio-phenyl.

When Ar is phenyl substituted by several different groups, examples are 5-bromo-2-methoxy-phenyl, 3-bromo-4,5-dimethoxy-phenyl, 6-bromo-3,4-dimethoxyphenyl or 4-methoxy-3-methyl-phenyl.

Among the preferred compounds of formula I are those wherein $R_1$ and $R_2$ are methyl and those wherein Z is hydrogen, chlorine or methyl, ethyl, propyl, isopropyl, methoxy, ethoxy or methylthio.

Examples of specific compounds of formula I are methyl 2-iso-propyl α-[(Z)-methoxy methylene]4-[(E)-styryl]-5-thiazolacetate, methyl α-[(Z)-methoxy methylene]-2-methyl-4-[(E)-styryl]-5-thiazolacetate and methyl α-[(Z)-methoxy methylene]-4-[(E)-styryl-5-thiazolacetate.

The novel process of the invention for the preparation of a compound of formula I comprises reacting a compound of the formula $$X-CH_2-CO-CH_2CH_2-COOR_1 \qquad II$$

in which X is chlorine or bromine and $R_1$ has the above meaning with a trialkyl phosphate of the formula $$(R_3O)_3P \qquad III$$

in which $R_3$ is methyl or ethyl to form a phosphonate of the formula

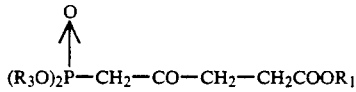

reacting the latter in the presence of a base with an aldehyde of the formula $$AR-CHO \qquad V$$

in which Ar has the above meaning to obtain a compound of the formula $$Ar-CH=CH-CO-CH_2-CH_2-COOR_1 \qquad VI$$

reacting the latter with a trialkyl chlorosilane of the formula $$R_4R_5R_6SiCl \qquad VII$$

in which $R_4$, $R_5$ and $R_6$ are individually alkyl of 1 to 4 carbon atoms to form a silylated enol ether of the formula $$Ar-CH=CH-C(OSiR_4R_5R_6)=CH-CH_2-COOR_1 \qquad VIII$$

brominating the latter to form a compound of the formula $$Ar-CH=CH-CO-CHBr-CH_2-COOR \qquad IX$$

reacting the latter either with a compound of the formula $$Z_1-CS-NH_2 \qquad X$$

in which $Z_1$ is hydrogen or alkyl of 1 to 6 carbon atoms to form a product of the formula

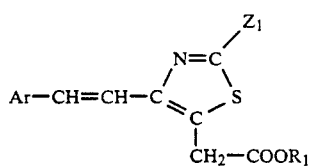 XI₁ or with a product of the formula

Alk₁—O—CS—NH₂  XII in which Alk₁ is alkyl of 1 to 4 carbon atoms to form a 2-thiazolinone derivative of the formula

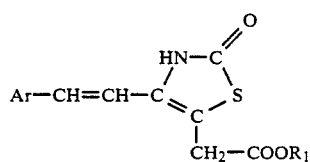 XIII reacting the latter with a chlorination reagent of the carbonyl functions to obtain a compound of the formula

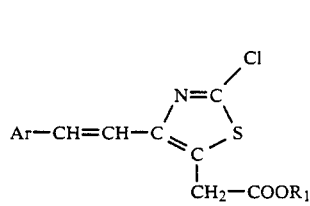 XI₂ optionally reacting the latter *either* with a base of the formula $Z_3^- \; M^+$  XIV in which $Z_3^-$ is an alcoholate anion and $M^+$ is an ammonium cation or an alkali metal cation to obtain a compound of the formula

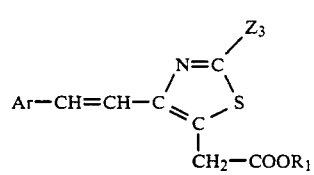 XI₃ or with a dithiocarbamate of the formula

NH₂—CS—S⁻ M³⁰  XV to obtain a 2-thiazolinethione derivative of the formula

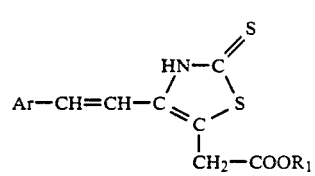 XVI condensing a compound of formulae XI₁, XI₂, XI₃ or XVI in the presence of a base with a dimethylformamide acetal of the formula Me₂N—CH(OR₇)₂  XVII in which R₇ is alkyl of 1 to 6 carbon atoms to obtain respectively a compound of the formulae

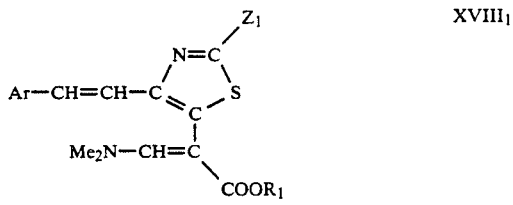 XVIII₁

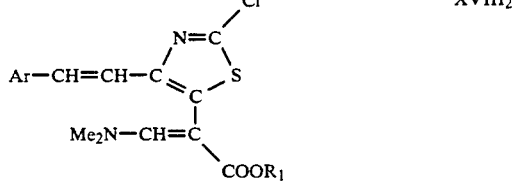 XVIII₂

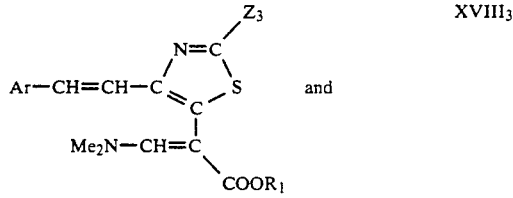 XVIII₃ and

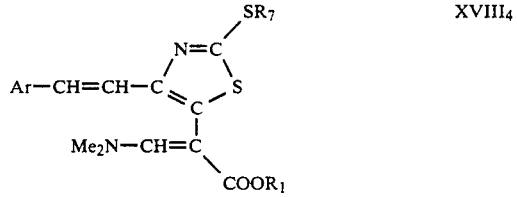 XVIII₄ which products correspond to a compound of the formula

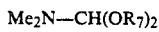 XVIII in which Z, Ar and R₁ have the above meaning subjecting the latter to a hydrolysis reaction to obtain a compound of the formula

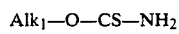 XIX and subjecting the latter to an etherification reaction to obtain a compound of formula I.

In a preferred method of the process, the reaction of products of formulae II and III to obtain a compound of formula IV is effected under the standard conditions of the so-called Arbuzov reaction, a known chemical reaction described generally in: "Pure and Applied Chemistry", Volume 9, pages 307 to 335, (1964). The preparation of the products of formula VI takes place under the standard conditions of the so-called Horner-Emmons reaction, a known chemical reaction and described generally in Chemical Reviews Volume 74, Pages 87 to 99, (1974).

The trialkyl chlorosilane used for the synthesis of the silylated enol ether of formula VIII may be trimethyl chlorosilane or tert-butyl dimethyl chlorosilane and the reaction is carried out in the presence of a nitrogenous base such as 1,5-diaza-5-bicyclo-[5,4,0]-undecene (DBU) or 1,5-diaza-5-bicyclo-[4,3,0]-nonene (DBN). The product of formula VIII is brominated without being purified beforehand by a standard bromination agent such as bromine or N-bromo succinimide (NBS) and the cyclization reaction into the product of formula XI takes place in an alcoholic medium, for example in methanol or ethanol.

The preparation of the products of formula XIII is carried out by the action of ethyl thiocarbamate on the product of formula IX in methanol or ethanol and the chlorination into the product of formula $XI_2$ is carried out by the action of phosphoryl chloride in the presence of a nitrogenous base such as 2,6-lutidine. The alcoholate of formula XIV used to obtain the product of formula $XI_3$ is for example sodium methylate or sodium ethylate and the dithiocarbamate used for the preparation of the product of formula XVI is ammonium dithiocarbamate. The etherification of the product of formula XIX is carried out with an alkyl halide such as methyl iodide and the preparation of the products of formula I from the products of formula XVIII can be carried out without isolating the intermediate product of formula XIX.

The products of formula II can be prepared from 4-oxo pentanoic acid (or levulinic acid) which is a commercial product, by esterification of this acid followed by a halogenation in the α-position of the carbonyl function as is described further on in the preparation of methyl 5-bromo-4-oxo pentanoate. Some products of formula II are known and their preparation is described in: Pichat et al, Bulletin de la Societe Chimique de France (1956), page 1,750; Rappe, Arl. Kemi, Volume 14, (1959), pages 467 to 469; Dannenberg et al, Chemisches Bericht, Volume 89, (1956), pages 2,242 to 2,252; Ratusky et al, Collect. Volume 23, (1958), pages 467 to 476. The products of formula III and most of the products of formula V are commercial products.

The products of formulae IX, XII, $XI_2$, $XI_3$, XIII, XVI, XVIII and XIX are new and are also an object of the present invention.

The novel fungicidal compositions of the invention are comprised of a fungicidally effective amount of at least one compound of formula I and an inert carrier. The compositions may be in the form of powders, granules, suspensions, emulsions, solutions or other preparations usually used in these preparations.

Examples of the carriers are a vehicle and/or an ionic or nonionic surfactant to ensure a uniform dispersion of the components of the mixture. The vehicle used can be a liquid such as water, alcohol, hydrocarbons or other organic solvents, a mineral, animal or vegetable oil, a powder such as talc, clays, silicates, kieselghur.

The compositions of the invention have useful fungicide properties which make them useful for protection with regard to pathogenic fungi and may be used for the protection of plants, the protection of premises or the protection of animals. These properties can also be used in hygiene and human and animal medicine.

The compositions of the invention are useful to combat very many phytopathogenic fungi, particularly *Erisyphe graminis, Sphaerotheca macularis, Sphaerotheca fuliginea, Podosphaera leucotricha, Uncinula necator, Helminthosporium* sp., *Rhynchosporium* sp., *Pseudocercosporella herpotrichoides* and *Gaeumannomyces graminis, Ustilago* sp., *Cercospora arachidicola* and *Cercosporidium personathum, Cercospora* sp., *Botrytis cinerea, Alternaria* sp., *Venturia inaequalis, Plasmopara viticola, Bremia lactucae, Peronospora* sp., *Pseudoperonospora humuli, Pseudoperonospora cubensis, Phytophtora* sp., infestans, *Phytophthora* sp., *Puccinia recondita, Thanatephorus cucumeris, Rhizoctonia* sp., or also fungi or yeasts affecting human health such as *Candida albicans* or *Trychophyton* sp.

The novel method of the invention for combatting fungi comprises contacting the fungi with a fungicidally effective amount of at least one compound of formula I.

In the following examples, there are described several preferred embodiments to illustrate the invention. However, it should be understood that the invention is not intended to be limited to the specific embodiments.

EXAMPLE 1

Methyl 2-isopropyl-α-(Z)-methoxymethylene]-4{-(E)-styryl]-5-thiazolacetate

STEP A: Methyl 5-(diethoxy phosphoryl)-4-oxo-pentanoate 10.5 ml of triethyl phosphite were added to 12.54 g of methyl 5-bromo-4-oxo-pentanoate and the mixture was heated at 140° C. with stirring. After reflux for one hour, the ethyl bromide formed was distilled off. After rectification under reduced pressure, 13.5 g of a colorless oil were obtained with a boiling point of 155° C. at 0.1 mm Hg.

STEP B: Methyl (E)-4-oxo-6-phenyl-5-hexenoate

A solution of 2.66 g of the phosphonate of Step A in 25 ml of tetrahydrofuran was added at 0° C. to 0.48 g of sodium hydride at 50% in oil in 20 ml of tetrahydrofuran, and the mixture was stirred for 30 minutes at 0° C. Then, 1.06 g of benzaldehyde and 15 ml of tetrahydrofuran were added and the mixture was allowed to return to 20°–21° C. with stirring for two hours, then it was poured into a 2N hydrochloric acid solution. After extraction with methylene chloride, the organic phase was dried over sodium sulfate, filtered and the filtrate was evaporated to dryness. The residue was chromatographed on silica and eluted with a hexane-ethyl acetate mixture (7-3) to obtain after evaporation of the solvent and drying, 1.1 g of crystals of the desired compound melting at 54.5° C. Thin layer chromatography; Rf=0.23 [eluant: hexane—ethyl acetate (7-3)].

| Infrared Analysis ($CHCL_3$ | |
|---|---|
| non-conjugated ester | 1735 $cm^{-1}$ |
| conjugated ketone | 1691 $cm^{-1}$ |
| aromatic ring | 1497, 1578, 1612 and 1625 $cm^{-1}$ |
| bond double in E configuration | 1667 and 989 $cm^{-1}$ |

| NMR analysis (CDCl₃) ppm | |
| --- | --- |
| CH₃ | 3.67; |
| CH₂'s | 2.53 to 3.13; |
| Ethylenic protons in E configuration | 6.55 and 6.82 and 7.43 and 7.70 J = 16 Hz; |
| aromatics | 7.17 to 7.67. |

STEP C: Methyl 6-phenyl-4-[(trimethylsilyl)-oxy]-hexa-3,5-dienoate 3 g of the product of Step B, 45 ml of diethyl ether and 2.2 ml of trimethylchlorosilane were mixed together and after the mixture was cooled to 0° C., then 2.5 ml of 1,5-diaza-5-bicyclo-[5,4,0]-undecene (DBU) and 20 ml of diethyl ether were added. The mixture was stirred while allowing the temperature to rise to 20° to 21° C. for one hour. After filtration, the ether was evaporated off to obtain 4.2 g of the desired product which was used as is in the following step.

STEP D: Methyl 3-bromo-4-oxo-6-phenyl-5-hexenoate

A mixture of 4.2 g of the product of Step C., 40 ml of tetrahydrofuran and 2.7 g of N-bromo-succinimide was cooled to 0° C. and stirred for one hour at this temperature, then brought to dryness. The residue was chromatographed on silica, eluting with a hexane-ethyl acetate mixture (8-2) to obtain 1.9 g of the expected product. Thin layer chromatography; Rf=0.28 [eluant: hexane-ethyl acetate (8-2)].

| Infrared Analysis: (CHCl₃) | |
| --- | --- |
| non-conjugated ester | 1734 cm⁻¹ |
| conjugated ketone, ring aromatic and double bond | complex with peaks at 1498, 1578, 1612, 1668 and 1692 cm⁻¹ |

| NMR Analysis: (CDCl₃) 60 mHz ppm | |
| --- | --- |
| CH₃ | 3.73 |
| —CH₂—COOCH₃ | 2.78–2.88 and 3.06–3.17 |
| CHBr | 4.86 4.97 and 4.99–5.10 |
| Ethylenic protons in E configuration | 6.83–7.09 and 7.68–7.93 |
| Aromatics | 7.28 to 7.90 |

STEP E: Methyl 2-isopropyl-4-[(E)-styryl]-5-thiazolacetate 6 g of the product of Step D were mixed with 60 ml of methanol and 2.1 g of 2-methyl propanethioamide (described in European Patent Application No. 0,402,246) and the mixture was refluxed for 5 hours. The mixture was allowed to return to 20° to 25° C., stirred for 16 hours, then brought to dryness. The residue was chromatographed on silica, eluting with a hexane-ethyl acetate mixture (8-2) to obtain after evaporation of the solvents, 1.75 g of the desired product. Thin layer chromatography; Rf=0.3 (eluant: hexane-ethyl acetate (8-2)].

| Infrared Analysis: (CHCl₃) | |
| --- | --- |
| non-conjugated ester | 1734 cm⁻¹ |
| Aromatic, C=C, C=N | 1490, 1520, 1576, 1600 and 1610 cm⁻¹ |
| Double bond in E configuration | 964 cm⁻¹ |

| NMR Analysis: (CDCl₃, 250 MHz) | |
| --- | --- |
| CH—(CH₃)₂ | 1.42 ppm (doublet; J=7Hz); |
| C$\underline{H}$—(CH₃)₂ | 3.31 ppm; |
| CO₂C$\underline{H}$₃ | 3.75 ppm; |
| C$\underline{H}$₂—CO₂CH₃ | 3.88 ppm; |
| Ethylenic proton in beta position of the styryl radical; | 7.00 ppm (doublet; J=16Hz) |
| Ethylenic proton in alpha position of the styryl radical; | 7.28 ppm (doublet) |
| Aromatics | 7.20 to 7.55 ppm. |

STEP F: Methyl α-[(dimethylamino)-methylene]-2-isopropyl-4-[(E)-styryl]-5-thiazolacetate A mixture of 3.1 g of the product of Step E and 30 ml of dimethylformamide dimethyl acetal was heated to 50° C. and after 5 hours at this temperature, the mixture was allowed to return to 20° to 25° C. The mixture was stirred for 16 hours and then was brought to dryness. The residue was chromatographed on silica, eluting with a hexane-ethyl acetate mixture (8-2) to obtain after evaporation of the solvents, 2 g of the desired product. Thin layer chromatography; Rf=0.15 [eluant: hexane-ethyl acetate (8-2)]

| NMR Analysis (CDCl₃, 250 MHz) | |
| --- | --- |
| CH—(CH₃)₃ | 1.42–1.44 ppm; |
| N—(CH₃)₂ | 2.80 ppm; |
| C$\underline{H}$—(CH₂)₃ | 3.30 ppm; |
| CO₂C$\underline{H}$₃ | 3.66 ppm; |
| Ethylenic protons in alpha and beta positions of the styryl radical; | 6.83 ppm |
| C=C$\underline{H}$—N | 7.76 ppm |

STEP G: Methyl α-(hydroxy methylene)-2-isopropyl-4-(E)-styryl]-5-thiazolacetate 2 g of the enamine of Step F, 20 ml of tetrahydrofuran and 5 ml of a 2N hydrochloric acid solution were mixed together under nitrogen and left for 5 hours at 20° to 21° C. The tetrahydrofuran was evaporated off and the product was used as is for the following step.

STEP H: Methyl 2-isopropyl-α-[(Z)-methoxy methylene]-4-[(E)-styryl]-5-thiazolacetate The product of Step G was dissolved in 20 ml of acetone and then 3 ml of methyl iodide and 4 g of potassium carbonate were added. The mixture was stirred for 16 hours at 20° C. After bringing the mixture to dryness, the residue was chromatographed on silica, eluting with a hexane-ethyl acetate mixture (8-2) to obtain 1.3 g of the desired product. Thin layer chromatography; Rf=0.20 [eluant: hexane-ethyl acetate (8-2)].

| NMR Analysis: (CDCl₃, 250 MHz) | |
| --- | --- |
| CH—(CH₃)₂ | 1.44 ppm; |
| C$\underline{H}$—(CH₃)₂ | 3.32 ppm; |
| CO₂C$\underline{H}$₃OC$\underline{H}$₃ | 3.75 and 3.89 ppm; |
| one of the aromatic ethylenic protons and the other ethylenic proton; | 6.75 ppm (doublet; J=16Hz); 7.12 to 7.45 ppm |

-continued

NMR Analysis: (CDCl₃, 250 MHz)

| | |
|---|---|
| C=C$\underline{H}$—OCH₃ (Z) | 7.70 ppm |

Analysis: C₁₉H₂₁NO₃S; molecular weight = 343.444

| | % C | % H | % N | % S |
|---|---|---|---|---|
| Calculated: | 66.45 | 6.16 | 4.08 | 9.33 |
| Found: | 66.1 | 6.1 | 4.0 | 9.3 |

EXAMPLE 2

Methyl α-[(Z)-methoxy methylene]-2-methyl-4-[(E)-styryl]-5-thiazolacetate

STEP A: Methyl 2-methyl-4-[(E)-styryl]-5-thiazolacetate 6 g of the product of Step D of Example 1 were mixed with 60 ml of methanol and 1.5 g of thioacetamide and the mixture was refluxed for 3 hours. Then it was poured into water, neutralized with sodium bicarbonate and extracted with methylene chloride. The organic phase was dried over magnesium sulfate, filtered and evaporated to dryness. The residue was chromatographed on silica, eluting with a hexane-ethyl acetate mixture (7-3) to obtain after evaporation of the solvents, 2.4 g of the desired product. Thin layer chromatography; Rf=0.35 [eluant: hexane-ethyl acetate (7-3)].

NMR Analysis: (CDCl₃, 250 MHz)

| | |
|---|---|
| methyl in position 2 | 2.70 ppm; |
| CH₃ of the ester | 3.74 ppm; |
| C$\underline{H}_2$—CO₂CH₃ | 3.75 ppm; |
| Ethylenic protons | 6.39 ppm (doublet; J=15.5Hz) and 7.50 ppm (doublet; J=15.5Hz); |
| Aromatics | 7.26, 7.35 and 7.52 ppm |

STEP B: Methyl α-[(Z)-methoxy methylene]-2-methyl-4-[(E)-styryl]-5-thiazolacetate A mixture of 3 g of the product of Step A and 30 ml of dimethylformamide dimethyl acetal was refluxed for 5 hours and then allowed to return to 25° C. The mixture was evaporated to dryness and the residue was dissolved in 30 ml of tetrahydrofuran and 5 ml of a 2N hydrochloric acid solution. After standing for 3 hours at 25° C., 10 ml of water were added, followed by decanting and extracting with methylene chloride. The organic phase was dried over magnesium sulfate, filtered and evaporated to dryness. The residue was dissolved in 50 ml of acetone and 6 g of potassium carbonate and then 12 ml of methyl iodide were added. The mixture was stirred for 16 hours at 20 to 25° C. and evaporated to dryness. The residue was chromatographed on silica, eluting with a hexane-ethyl acetate mixture (7-3) to obtain 1.8 g of the desired product. Thin layer chromatography; Rf=0.20 [eluant: hexane-ethyl acetate (7-3)].

NMR Analysis (CDCl₃, 250 MHz)

| | |
|---|---|
| methyl in position 2 | 2.72 ppm; |
| methyl of the ester and the methoxy radical; | 3.75 and 3.91 ppm |
| ethylenic protons | 6.75 ppm (doublet; J = 16 Hz) and 7.30 ppm (doublet; J = 16 Hz); |
| aromatics | 7.19 to 7.50 ppm; |

-continued

NMR Analysis (CDCl₃, 250 MHz)

| | |
|---|---|
| Proton of the methylene radical | 7.71 ppm |
| [(Z) configuration of the double bond]. | |

Analysis: C₁₇H₁₇NO₃S; molecular weight = 315.390

| | % C | % H | % N | % S |
|---|---|---|---|---|
| Calculated: | 64.74 | 4.43 | 4.44 | 10.17 |
| Found: | 63.9 | 5.3 | 4.3 | 9.8 |

EXAMPLE 3

Methyl α-[(Z)-methoxy methylene]-4-[(E)-styryl]-5-thiazolacetate

STEP A: Methyl 4-[(E)-styryl]-5-thiazolacetate 8 g of the product of Step D of Example 1 were mixed with 80 ml of methanol and 1.8 g of thioformamide (described in European Patent application No. 0,042,246) and the mixture was refluxed for 4 hours. Then, it was poured into water and extracted with methylene chloride. The organic phase was dried over magnesium sulfate, filtered and evaporated to dryness. The residue was chromatographed on silica, eluting with a hexane-ethyl acetate mixture (8-2) to obtain after evaporation of the solvents, 2.5 g of the desired product. Thin layer chromatography; Rf=0.19 (eluant: hexane-ethyl acetate (8-2)].

NMR Analysis: (CDCl₃, 250 MHz)

| | |
|---|---|
| methyl of the ester | 3.76 ppm; |
| C$\underline{H}_2$—CO₂CH₃ | 3.96 ppm; |
| Ethlenic and aromatic protons | 7.06 ppm (doublet; J=16Hz) and 7.2 to 7.7 ppm; |
| Proton in position 2 of the thiazole. | 8.75 ppm |

STEP B: Methyl α-[(Z)-methoxy methylene]-4-[(E)-styryl]-5-thiazolacetate

A mixture of 2.5 g of the product of Step A and 25 ml of dimethylformamide dimethyl acetal was heated to 50° C. and after 4 hours at this temperature, the mixture was allowed to return to 25° C. The reaction mixture was evaporated to dryness and the residue was dissolved in 30 ml of tetrahydrofuran and 5 ml of an aqueous solution of 2N hydrochloric acid. After standing for 2 hours at 25° C., the mixture was decanted followed by extraction with methylene chloride. The organic phase was dried over magnesium sulfate, filtered and evaporated to dryness. The residue was dissolved in 30 ml of acetone and 4 g of potassium carbonate and 6 ml of methyl iodide were added. The mixture was stirred for 16 hours at 20° to 25° C. and after filtering and evaporating to dryness, the residue was chromatographed on silica, eluting with a hexane-ethyl acetate mixture (7-3) to obtain 1.1 g of the desired product. Thin layer chromatography; Rf=0.17 [eluant: hexane-acetate of ethyl (7-3)].

NMR Analysis (CDCL₃, 250 MHz)

| | |
|---|---|
| Methyl of the ester and the methoxy radical; | 3.75 and 3.91 ppm |
| Ethylenic protons [(E) configuration] | 6.82 ppm (doublet; J = 16 Hz) and 7.56 ppm (doublet; J = 16 Hz); |

-continued

| NMR Analysis (CDCL₃, 250 MHz) | |
|---|---|
| Aromatics | 7.20 to 7.53 ppm |
| Proton of the methylene radical [(Z) configuration of the double bond]; | 7.75 ppm |
| Proton in position 2 of the thiazole | 8.83 ppm |

| Analysis: $C_{16}H_{15}NO_3S$; molecular weight = 301.363 | | | | |
|---|---|---|---|---|
| Calculated: | % C 63.77 | % H 5.02 | % N 4.65 | % S 10.64 |
| Found: | 63.2 | 5.0 | 4.3 | 10.5 |

EXAMPLE 4

Methyl 2-chloro-α-[(Z)-methoxy methylene]-4-[(E)-styryl]-5-thiazolacetate

STEP A: Methyl 2-oxo-4-[(E)-styryl]-5-thiazolacetate 20 g of the product of Step D of Example 1 were mixed with 200 ml of methanol and then 8.5 g of ethyl thiocarbamate were added. The mixture was refluxed for 4 hours and then allowed to return to 20° to 25° C. The mixture was poured into water and extracted with methylene chloride. The organic phase was dried over sodium sulfate, filtered and brought to dryness. The residue was taken up in isopropyl ether, then separated to obtain 8.7 g of the desired product melting at 164.2° C. Thin layer chromatography; Rf=0.11 [eluant: hexane-ethyl acetate (7-3)].

| NMR Analysis (DMSO, 250 MHz) | |
|---|---|
| methyl of the ester | 3.66 ppm; |
| C$\underline{H}_2$—CO₂CH₃ | 3.93 ppm; |
| Ethylenic and aromatic protons | 7.05 ppm and 7.3 to 7.56 ppm; |
| Proton of NH or OH | 11.45 ppm. |

STEP B: Methyl 2-chloro-4-[(E)-styryl]-5-thiazolacetate 6 g of the product of Step A were mixed with 24 ml of phosphorus oxychloride (POCl₃) and then 2.5 ml of 2,6-lutidine were introduced dropwise. After refluxing for 3 hours 30 minutes, the mixture was allowed to return to 20° to 25° C. The excess POCl₃ was eliminated under reduced pressure, and the reaction medium was poured into 40 ml of ice-cooled water and extracted with methylene chloride. The organic phase was dried over sodium sulfate, filtered and evaporated to dryness. The residue was chromatographed on silica, eluting with a hexane-ethyl acetate mixture (7-3) to obtain after evaporation of the solvents, 6 g of the desired product melting at 84.5° C. Thin layer chromatography; Rf=0.35 [eluant: hexane-ethyl acetate (7-3)].

| NMR Analysis: (CDCl₃, 250 MHz) | |
|---|---|
| methyl of the ester | 3.77 ppm; |
| C$\underline{H}_2$—CO₂CH₃ | 3.88 ppm; |
| an ethylenic proton [(E) configuration]; | 6.91 ppm (doublet; J=16Hz) |
| The other ethylenic proton and the aromatic protons. | 7.28 to 7.55 ppm |

STEP C: Methyl 2-chloro-α-[(dimethylamino)-methylene]-4-[(E)-styryl]-5-thiazolacetate A mixture of 5.9 g of the product of Step B and 55 ml of dimethylformamide dimethyl acetal was heated to 50° C. and after 4 hours at this temperature, the mixture was allowed to return to 25° C. The reaction mixture was evaporated to dryness and the residue was chromatographed on silica, eluting with a hexane-ethyl acetate mixture (7-3) to obtain 3.3 g of the desired product. Thin layer chromatography; Rf=0.18 [eluant: hexane-ethyl acetate (7-3)].

| NMR Analysis: (CDCl₃, 250 MHz) | |
|---|---|
| methyl of the dimethylamino radical | 2.86 ppm |
| methyl of the ester | 3.67 ppm; |
| an ethylenic proton [(E) configuration]; | 6.78 ppm (doublet; J = 16 Hz) |
| the other ethylenic proton and the aromatic protons. | 7.21 to 7.51 ppm |

STEP D: Methyl 2-chloro-α-[(Z)-methoxy methylene]-4-[(E)-styryl]-5-thiazolacetate 3 g of the product of Step C were mixed with 30 ml of tetrahydrofuran and then 5 ml of a 2N hydrochloric acid solution were added. The mixture stood at 20° to 25° C. for 5 hours and was then poured into water and extracted with methylene chloride. The organic phase was dried over magnesium sulfate, filtered and evaporated to dryness. The residue was dissolved in 20 ml of acetone and 3 g of potassium carbonate and then 8 ml of methyl iodide were added. When the reaction was finished, filtration was carried out, followed by evaporation to dryness. The residue was chromatographed on silica, eluting with a methylene chloride-hexane mixture (6-4) to obtain after evaporation of the solvents, 0.34 g of product A and 0.80 g of product B.

Product A: Thin layer chromatography; Rf=0.17 [eluant: methylene chloride-hexane (6-4)].

| NMR Analysis: (CDCL₃, 250 MHz) | |
|---|---|
| methyl of the ester and the methoxy; | 3.77 and 3.93 ppm |
| One of the ethylenic protons [(E) configuration]; | 6.67 ppm (doublet; J = 16 Hz) |
| The other ethylenic proton and the aromatics; | 7.20 to 7.60 ppm |
| Proton of the methylene [(Z) configuration of the double bond]. | 7.73 ppm |

| Analysis: $C_{16}H_{14}ClNO_3S$; molecular weight = 335.808 | | | | | |
|---|---|---|---|---|---|
| Calculated: | % C 57.23 | % H 4.20 | % Cl 10.56 | % N 4.17 | % S 9.55 |
| Found: | 57.1 | 4.1 | 10.8 | 4.0 | 9.3 |

EXAMPLE 5

Methyl 2-chloro-α-[(E)-methoxy methylene]-4-[(E)-styryl]-5-thiazolacetate

Product B of Step D of Example 4 melted at 110° C.
Product B: Thin layer chromatography; Rf=0.11 [eluant: methylene chloride-hexane (6-4)].

NMR Analysis: (CDCl₃, 250 MHz)

| | |
|---|---|
| methyl of the ester and the methoxy; | 3.77 and 4.00 ppm |
| one of the ethylenic protons [(E) configuration]; | 6.89 ppm (doublet; J = 16 Hz) |
| the other ethylenic proton the aromatics; | 7.20 to 7.55 ppm |
| proton of the methylene radical [(E) configuration of the double bond]. | 6.79 ppm |

Analysis: $C_{16}H_{14}ClNO_3S$; molecular weight = 335.808

| | % C | % H | % Cl | % N | % S |
|---|---|---|---|---|---|
| Calculated: | 57.23 | 4.20 | 10.56 | 4.17 | 9.55 |
| Found: | 57.3 | 4.2 | 11.0 | 4.0 | 9.3 |

Preparation of methyl 5-bromo-4-oxo pentanoate

STEP A: methyl 4-oxo pentanoate

A solution of 300 g of 4-oxo pentanoic acid (levulinic acid), 300 ml of methanol and 2 ml of 97% sulfuric acid was stirred for 16 hours at 20° to 25° C. and then was evaporated to dryness. The residue was rectified under reduced pressure to obtain 290 g of the expected methyl ester with a boiling point of 87° to 88° C. at 16 mm Hg. Thin layer chromatography; Rf=0.13 [eluant: hexane-ethyl acetate (8-2)].

STEP B: Methyl 5-bromo-4-oxo pentanoate 100 g of the ester of Step A were mixed with 1600 ml of methanol and 2 ml of concentrated acetic acid and the mixture was heated to 40° C. Then 42 ml of bromine were introduced and the temperature was allowed to return to 25° C. with stirring. The mixture was evaporated to dryness and the residue was dissolved in 100 ml of water and neutralized with a saturated aqueous solution of sodium bicarbonate. After extraction with diethyl ether, the organic phase was dried over magnesium sulfate, filtered and brought to dryness. The residue was chromatographed on silica to obtain 133.6 g of the desired product. Thin layer chromatography; Rf=0.18 [eluant: hexane-ethyl acetate (8-2)].

BIOLOGICAL STUDY

Study of the Fungicide Activity a) *Plasmopara viticola* tests (Test A)

Young vine plants from shoots (Grenache N variety, clone 70) were cultivated in a greenhouse (daytime temperature: 30° C., nighttime temperature: 25° C.) in an earth/compost/sand mixture, (166 -⅓-⅓). Two days before the test, the plants were moved to a cultivation chamber (same temperature conditions, humidity: 60% in the day, 80% at night). The test product was dissolved in "matrix A" at a concentration of 500 ppm just before use. The treatment was carried out by spraying the solution on the leaves until maximum retention was achieved. The contamination was carried out with a suspension of zoosporanges of *Plasmopara viticola* taken immediately before the test (50,000 zoosporanges per ml). Drops of suspension (20 microliters) were deposited on the abaxial surface of the leaves. The plants were kept for 24 hours in an atmosphere saturated with moisture, and then returned to the humidity of the cultivation chamber (60% in the day, 80% at night).

The reading was carried out ten days after contamination, by measuring the development of islets of conidiophores on the abaxial surface of the leaves. The effectiveness of the product was calculated relative to a non-treated control.

b) *Erysiphe graminis* hordei tests (Test B)

Barley seeds (Pression variety) were germinated in an earth-compost-sand mixture (⅓-⅓-⅓) and cultivated in a greenhouse. The test products were dissolved in "matrix A" just before the test at a concentration of 500 ppm. The treatment was carried out by spraying the product solution on the 10-day old barley until maximum retention was achieved. The contamination by conidia of *Erysiphe graminis* hordei was carried out three days after the treatment. The plants were kept in an air-conditioned room (daytime temperature: 23° C., night-time temperature: 18° C). Seven days after contamination, the extent of the conidial covering on the first and second leaf of each plant was measured. The effectiveness of the product was calculated relative to a non-treated control.

c) *Puccinia recondita* tritici tests (Test C)

Wheat seeds (Festival variety) were germinated in an earth-compost-sand mixture (⅓-⅓-⅓). The plants were cultivated in a greenhouse and the products were dissolved in "matrix A" just before the test at a concentration of 500 ppm. The treatment was carried out by spraying the product solution on the 9-day old wheat plants until maximum retention was achieved. The contamination by uredospores of *Puccinia recondita* tritici was carried out the day after treatment. The plants were kept in an air-conditioned room (daytime temperature: 22° C., night-time temperature: 18° C). Seven days after the contamination, the density of spores on the first two leaves of each plant was measured and the effectiveness of the product was calculated relative to a non-treated control.

| | | Test B | | |
|---|---|---|---|---|
| EX. | Test A | 1st L | 2nd L | Test C |
| 1 | 90 | — | — | — |
| 2 | 90 | — | — | — |
| 3 | 100 | 80 | 30 | — |
| 4 | — | — | — | 70 |

These results were a good indication of the fungicide activity of the products of Examples 1 to 3 against BOTRYTIS CINEREA on vines, the product of the Example 3 against ERYSIPHE GRAMINIS HORDEI on barley and the product of the Example 4 against PUCCINIA RECONDITA TRITICI on wheat.

| Composition of matrix A: | |
|---|---|
| SOLVESSO 150 | 70.0 g |
| NAPSOL PM1 | 850.0 g |
| SURFAROX HRH 40C | 52.0 g |
| ECD 1604 | 28.0 g |
| | 1000.0 g |

Various modifications of the products and methods of the invention may be made without departing from the spirit or scope thereof and it is to be understood that the invention is intended to be limited only as defined in the appended claims.

What we claim is:

1. A compound of the formula
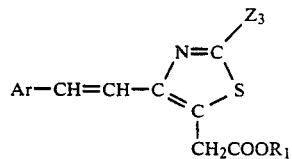
wherein Ar is phenyl optionally substituted with at least one member of the group consisting of halogen, methylenedioxy, phenyl, phenoxy, —$CF_3$ and alkyl, alkoxy and alkylthio of 1 to 6 carbon atoms, $Z_3$ is an alkoxy of one to 6 carbon atoms, $R_1$ is alkyl of 1 to 6 carbon atoms.
* * * * *